United States Patent [19]
Rivola et al.

[11] 3,974,216
[45] Aug. 10, 1976

[54] PROCESS FOR RECOVERING AMMONIUM ORGANIC SALTS FROM AQUEOUS SOLUTIONS

[75] Inventors: Luigi Rivola; Bruno Notari, both of San Donato Milanese, Italy

[73] Assignee: Snam Progetti S.p.A., San Donato Milanese, Italy

[22] Filed: Nov. 19, 1973

[21] Appl. No.: 417,357

[30] Foreign Application Priority Data
Nov. 29, 1972  Italy .................................. 32207/72

[52] U.S. Cl. ............................. 260/541; 260/527 R
[51] Int. Cl.² ........................................ C07C 51/42
[58] Field of Search ......... 260/541, 540, 542, 527 R

[56] References Cited
UNITED STATES PATENTS

| | | | |
|---|---|---|---|
| 2,895,990 | 7/1959 | Larrison et al. | 260/540 |
| 3,123,632 | 3/1964 | Katzschmann | 260/540 |

*Primary Examiner*—Vivian Garner
*Attorney, Agent, or Firm*—Ralph M. Watson

[57] ABSTRACT

An ammonium organic salt is recovered from an aqueous solution in which it is contained at a concentration in the range from 0.2% to the salt solubility limit by atomizing the solution in hot air at a temperature in the range of 100° to 150°C.

2 Claims, No Drawings

PROCESS FOR RECOVERING AMMONIUM ORGANIC SALTS FROM AQUEOUS SOLUTIONS

The present invention relates to a process for recovering ammonium organic salts from aqueous solutions containing same.

More particularly the present invention relates to a process for recovering ammonium organic salts from the aqueous solutions thereof which have been industrial wastes, such as, for instance the ammonium acetate contained in the exhaust wash liquids discharged during the preparation of alumina base catalysts. Some industrial processes do not include provision for the treatment of the wash liquids which, therefore, are discharged as waste and give rise to the drawbacks caused by pollution and also, as in the process for the preparation of catalyst, increase the cost thereof because of the necessity of always feeding new materials.

The aforesaid drawbacks are overcome through the process of our invention which makes it possible to treat polluting substances so that they are not discharged waste and, because of the contemporaneous recovery of the ammonium organic salt, allows its recycle as feed.

Moreover it is clear that the foregoing remarks respecting ammonium acetate can be extended to any ammonium salt of organic nature, contained in aqueous solution irrespective of source. Our interest in the spheroidal alumina field has prompted us to choose the aforesaid process as exemplary: no problem exists which would prevent those skilled in the art from making our process of general application.

The process according to the present invention consists fundamentally in atomizing, in hot air (100°–150°C), the aqueous exhaust solution derived from industrial wash water.

The ammonium salt concentration of the solution can range from 0.2% up to the solubility limit, e.g., from 1 to 40% by weight. While atomizing, the salts contained therein are separated: the mineral salts are collected after the dust removal cyclone, while the organic salts are collected in a series of fumes removal apparatus. The greater part of the organic salt (95–99%) is recovered from the solution coming from the recycle water through the fumes removal apparatus. Other gases may be collected in a following gas adsorbing system. All the working parameters will be more clearly understood by examining the following examples, hereinafter reported for better illustrating the invention, however, without limiting the purposes thereof.

EXAMPLE 1

An aqueous solution having the following composition by weight:

| | |
|---|---|
| $NH_4Cl$ | 5% |
| $CH_3COONH_4$ | 5% |
| $NH_3$ | 1.5% | corresponding to the composition of the first washing liquid of spheroidal gel alumina (obtained according to Italian Patent No. 753,063) was atomized in a Niro Atomizer A/S. The atomization was carried out at a turbine output gas temperature of 130°C and at an air feed temperature one of 350°C. The air flowing from the atomizer was sent to a removal columns system wherein water was circulated in a closed circuit.

The aforesaid solution as fed by means of a volumetric pump of the screw type at a 15 1/h flow rate.

The following results were obtained:

a. the solid, which was formed in the room and was recovered in the fumes removal cyclone, was $NH_4Cl$ with a $NH_4COOCH_3$ content lower than the limits of analytical accuracy. The $NH_4Cl$ recovery was more than 95% of the starting content;

b. the washing liquid of the gas removal columns contained only $NH_4COOCH_3$ at a maximum concentration of 40%. By working at 50°C temperature the recovery yield was higher than 95% with respect to the starting content;

c. the gases coming out from the washing system contained the most of the $NH_3$ which was recovered by means of a recovery device based on molecular sieves.

The aqueous solution of $NH_4COONH_3$ thus obtained (point b) coming from the gas washing column could be utilized directly for a following gelling phase, by mixing it with an aluminium chlorohydroxide solution according to what is disclosed in the aforesaid patent.

EXAMPLE 2

The operations of the preceding example was carried out starting from an aqueous solution having the following composition by weight

| | |
|---|---|
| $NH_4Cl$ | 15% |
| $CH_3COONH_4$ | 15% |

The results were similar to the ones of example 1, i.e. $NH_4COOCH_3$ was completely separated from chloride; the ammonium acetate solution recovered in the washing waters of the removal apparatus could reach a 40% concentration and, as such, could be directly utilized for following purposes.

What is claimed is:

1. Process for recovering ammonium acetate from an aqueous solution containing the same in a concentration in the range from 0.2% to the salt solubility limit consisting in atomizing the aqueous solution in hot air at a temperature in the range from 100° to 150°C.

2. Process according to claim 1 characterized in that the solution concentration is in the range from 1 to 40% by weight.

* * * * *